(12) United States Patent
Woon et al.

(10) Patent No.: US 12,232,658 B2
(45) Date of Patent: Feb. 25, 2025

(54) ANTI-PLUME TOILET SEAT AND TOILET LID

(71) Applicant: Kohler Co., Kohler, WI (US)

(72) Inventors: Taiwoon Woon, Singapore (SG); Jeffrey T. Laundre, Sheboygan, WI (US)

(73) Assignee: Kohler Co., Kohler, WI (US)

( * ) Notice: Subject to any disclaimer, the term of this patent is extended or adjusted under 35 U.S.C. 154(b) by 229 days.

(21) Appl. No.: 17/678,254

(22) Filed: Feb. 23, 2022

(65) Prior Publication Data

US 2022/0279993 A1    Sep. 8, 2022

Related U.S. Application Data

(60) Provisional application No. 63/157,931, filed on Mar. 8, 2021.

(51) Int. Cl.
*A47K 13/10* (2006.01)
*A61L 2/26* (2006.01)
*A61L 101/26* (2006.01)

(52) U.S. Cl.
CPC .............. *A47K 13/105* (2013.01); *A61L 2/26* (2013.01); *A61L 2101/26* (2020.08)

(58) Field of Classification Search
CPC ...... A47K 13/105; A61L 2/26; A61L 2021/26
USPC .......................................................... 4/246.1
See application file for complete search history.

(56) References Cited

U.S. PATENT DOCUMENTS

| | | | | |
|---|---|---|---|---|
| 5,065,460 A | * | 11/1991 | Currin | A47K 13/105 4/246.1 |
| D385,341 S | * | 10/1997 | Ouzounian | D23/311 |
| 6,634,032 B1 | * | 10/2003 | Janik | A47K 13/105 4/246.1 |
| 6,918,142 B1 | * | 7/2005 | Wainwright | A47K 13/105 4/246.1 |
| 7,272,862 B1 | * | 9/2007 | Ellington | A41D 27/145 2/232 |
| 8,132,272 B1 | * | 3/2012 | Esposito | A47K 13/105 4/246.1 |

(Continued)

FOREIGN PATENT DOCUMENTS

CN    202714786 U    2/2013
CN    204071927 U    1/2015

(Continued)

OTHER PUBLICATIONS

Chinese Office Action from Chinese Patent Application No. 2023102700972920, dated Oct. 27, 2023, 14 pages. (including English summary).

*Primary Examiner* — Huyen D Le
(74) *Attorney, Agent, or Firm* — Lempia Summerfield Katz LLC

(57) ABSTRACT

The present disclosure provides a toilet seat including a rim; and a tab made from an antibacterial material and configured to be attached to the rim as a touch point for a user to open or close the toilet seat. The present disclosure provides a toilet including a toilet bowl; a toilet seat comprising a rim and pivotably attached to the toilet bowl; a toilet lid pivotably attached to the toilet bowl or the toilet seat; and a first tab made from an antibacterial material and configured to be attached to the toilet seat as a first touch point for a user to open or close the toilet seat.

6 Claims, 20 Drawing Sheets

(56) References Cited

U.S. PATENT DOCUMENTS

| | | | |
|---|---|---|---|
| 9,907,443 B1 * | 3/2018 | Vinal | ............... A47K 13/26 |
| 2007/0143910 A1 | 6/2007 | Lauffer | |
| 2014/0000018 A1 | 1/2014 | Chandler et al. | |
| 2017/0027397 A1 | 2/2017 | Matthews | |

FOREIGN PATENT DOCUMENTS

| | | |
|---|---|---|
| CN | 204743981 U | 11/2015 |
| CN | 106609642 A | 5/2017 |
| CN | 210095608 U | 2/2020 |
| TW | 586400 U | 5/2004 |
| TW | M458191 U | 8/2013 |
| TW | M484396 U | 8/2014 |

* cited by examiner

ANTI-PLUME TOILET SEAT AND TOILET LID

CROSS REFERENCE TO PRIOR APPLICATION

This application claims priority benefit of Provisional Application No. 63/157,931 filed Mar. 8, 2021, the content of which is hereby incorporated by reference in its entirety.

FIELD

The present disclosure relates to an anti-plume toilet seat and an anti-plume toilet lid. In particular, the present disclosure relates to tabs made from an antibacterial material for use in a toilet seat and a toilet lid and an anti-plume toilet seat an anti-plume toilet lid comprising the tabs.

BACKGROUND

A toilet plume is a dispersal of excrement particles as a result of flushing a toilet. The excrement particles may contain high concentrations of pathogens carried by toilet users who have been infected with diseases, e.g. pandemic diseases like coronavirus, norovirus, swine flu etc. or bacterial diseases. The pathogens contained in the excrement particles sprayed out of a toilet bowl may spread via an airborne transmission because the flushing may produce infectious aerosols. The pathogens may also spread via a direct contact because the pathogens carried in the aerosols may settle and survive on surfaces, e.g. the toilet seat, the toilet lid etc. Thus, when subsequent users touch by hand the toilet seat or the toilet lid contaminated by the pathogens of previous users, the subsequent users are subject to high risks of getting infected with the pathogens.

Some medical researches reveal that copper is an antibacterial material. The copper may kill or reduce pathogens by destroying the nucleic acids or reproductive blueprints of the pathogens. However, current toilets in the art merely use the copper for decorative and aesthetic purposes. For example, the whole toilet, the toilet seat, or the toilet lid is made from the copper instead of the plastic. However, the copper is a more expensive than the plastic and thus makes the toilets very costly.

Therefore, there is a need to provide a more cost-efficient toilet seat or toilet lid to reduce or eliminate the risks for the users to get infected with the pathogens when opening or closing the toilet seat or toilet lid. There is also a need to provide a device having a simple structure and configured to provide a touch point for the users so that the device may be easily manufactured and installed on the current toilets and the contaminated device may be easily replaced with a new device. There is also a need to provide a device made with a robust material, which may be sanitized or cleaned repeatedly with toilet cleaning agents e.g. nitric acid, to further reduce or eliminate the risks for the users to get infected with the pathogens.

Additionally, in many countries including the United States, the toilets in the public bathrooms are designed to include a gap in the toilet seats, in other words, in U-shape ("open-front seat"). In the United States, such an open-front seat is required by the local rules and regulations for the hygiene reason. The open-front seat is designed to avoid touching the seat with private parts of the users when the users sit on the toilet. The open-front seat is also designed to allow the female users to wipe their private parts more easily. The open-front seat is also designed to eliminates an area that could be contaminated by urine when the male users use the toilet. However, the gap in the toilet seat leaves a space between the toilet lid and the toilet bowl. The excrement particles containing the pathogens may escape from the gap and spread in the form of the aerosols and thus may increase the risks for the users to get infected with the pathogens when the toilet is flushed.

Therefore, there is a need to provide a device disposed on the toilet lid in a manner that provides securely close the space between the toilet lid and the toilet bowl, while maintaining the above-mentioned functions of the open-front seat.

SUMMARY

In one aspect, the present disclosure provides a toilet seat comprising: a rim; and a tab made from an antibacterial material and configured to be attached to the rim as a touch point for a user to open or close the toilet seat.

In another aspect, the present disclosure provides a toilet comprising: a toilet bowl; a toilet seat pivotably attached to the toilet bowl; a toilet lid pivotably attached to the toilet bowl or the toilet seat; a first tab made from an antibacterial material and configured to be attached to the toilet seat as a first touch point for a user; a second tab made from an antibacterial material and configured to be attached to the toilet lid as a second touch point for the user; at least one protrusion disposed at a lower surface of the toilet seat and configured to form a first gap between the toilet bowl and the toilet seat; at least one protrusion disposed at a lower surface of the toilet lid and configured to form a second gap between the toilet seat and the toilet lid; first and second frames respectively configured to seal the first and second gaps. The first tab is attached to the toilet seat via the first frame and the second tab is attached to the toilet lid via the second frame.

In another aspect, the present disclosure provides a method for assembling a toilet, the method comprising installing a first frame on a lower surface of a toilet seat so as to seal a first gap between a toilet bowl and the toilet seat when the toilet seat is in a closed position with respect to the toilet bowl. The method also comprises installing a second frame on a lower surface of a toilet lid so as to seal a second gap between the toilet seat and the toilet lid when the toilet lid is in a closed position with respect to the toilet seat. The method also comprises attaching a first tab to the toilet seat via the first frame by inserting an insert portion of the first tab into a first groove of the first frame. The method also comprises attaching a second tab to the toilet lid via the second frame by inserting an insert portion of the second tab into a second groove of the second frame.

DETAILED DESCRIPTION

Figure 1:
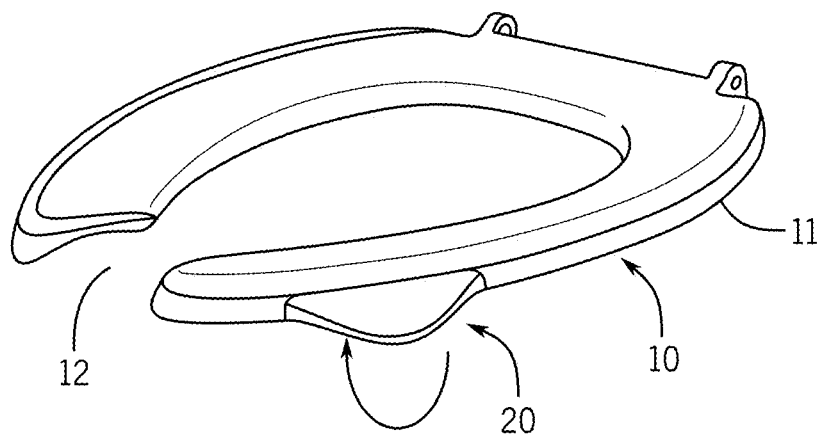
FIG. 1 is a perspective view of a toilet seat comprising a tab according to a first embodiment of the present disclosure.

Hereinafter, specific embodiments of the present disclosure are described in detail with reference to the drawings. In adding the reference numerals to the elements of each drawing, it should be noted that the identical or equivalent element is designated by the identical numeral even when they are displayed on other drawings. Further, in describing the embodiments of the present disclosure, a detailed description of well-known features or functions has been omitted in order not to unnecessarily obscure the gist of the present disclosure.

Unless otherwise defined, all terms used herein, including technical and scientific terms, have the same meaning as those generally understood by those having ordinary skill in the art to which the present disclosure pertains. Such terms as those defined in a generally used dictionary are to be interpreted as having meanings equal to the contextual meanings in the relevant field of art, and are not to be interpreted as having ideal or excessively formal meanings unless clearly defined as having such in the present application.

First Embodiment

Figure 2:
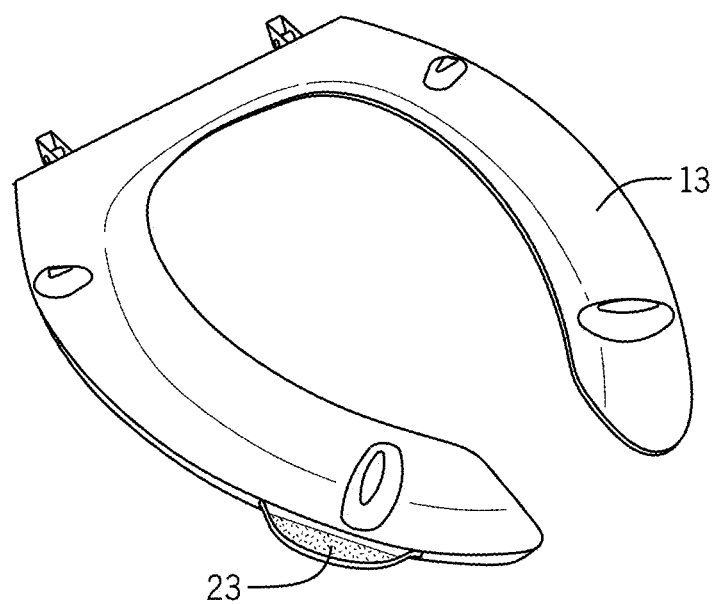
FIG. 2 is a bottom view of the toilet seat comprising the tab according to the first embodiment of the present disclosure.
Figure 3:
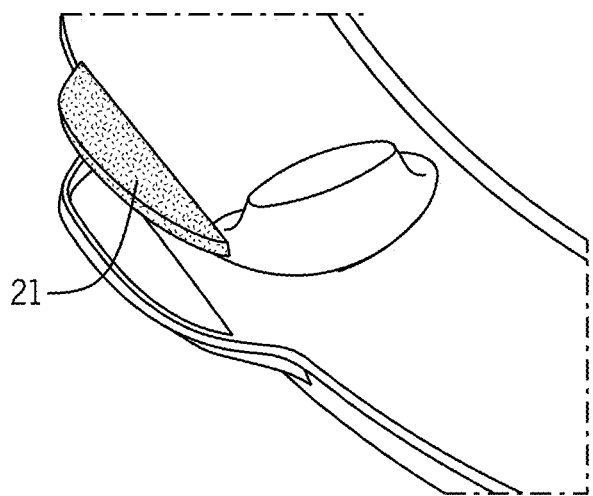
FIG. 3 is an enlarged view of the toilet seat comprising the tab according to the first embodiment of the present disclosure.

FIG. 1 is a perspective view of a toilet seat comprising a tab according to a first embodiment of the present disclosure. FIG. 2 is a bottom view of the toilet seat comprising the tab according to the first embodiment of the present disclosure. FIG. 3 is an enlarged view of the toilet seat comprising the tab according to the first embodiment of the present disclosure.

Referring to FIG. 1 to FIG. 3, a toilet seat 10 is configured to installed on a toilet bowl (not shown in the figures). The toilet seat 10 comprises a U-shaped rim 11 having a gap 12 disposed at a front end of the rim 11 ("open-front seat"). The front end of the rim 11 is defined by an end facing a toilet user. However, in another embodiment, the toilet seat 10 may also be a closed-front seat without the gap 12. A tab 20 is disposed on the toilet seat 10 and extends radially outwards from the rim 11. Thus, the tab 20 forms a touch point for the toilet user when the toilet user lifts up or drops down the toilet seat 10.

The tab 20 is made from an antibacterial material that may reduce or completely kill the pathogens deposited on the tab 20 after the toilet user touches the tab 20. In this embodiment, the tab 20 is made from metal copper by inlaying the copper in the tab 20 so that the copper material is invisible to the toilet user from the appearance of the tab 20. However, the antibacterial material is not limited to the copper. In another embodiment, any other antibacterial material may be used.

In this embodiment, the tab 20 is disposed on a lower surface 13 of the toilet seat 10. A copper tab sheet may be inmolded to form the tab 20 on the lower surface 13 of the toilet seat 10. Any attachment technologies may be used. Therefore, the tab 20 may reduce or eliminate the risks for the toilet users to get infected with the pathogens when opening or closing the toilet seat 10.

The tab 20 is made from a small piece of the copper tab sheet. The tab 20 may be in any shapes and sizes that offer the toilet user a firm grip when the user lifts up or drops down the toilet seat 10. In this embodiment, the tab 20 comprises a curved rim 21 and thus the tab 20 is in a substantially semicircle shape. The tab 20 may be in any shape and size suitable for a normal human hand size, e.g. having an ergonomic design.

In this embodiment, only a small piece of the tab 20 is made from the copper material. Neither the toilet seat nor the toilet lid is made from the copper material. Also, the tab 20 is compatible with any types of the current toilet seats and thus no extra process is required for manufacturing the toilet seat itself. Therefore, these advantages significantly reduce the costs for manufacturing the tab 20 and the toilet seat 10 comprising the tab 20 according to this embodiment.

Second Embodiment

Figure 4:
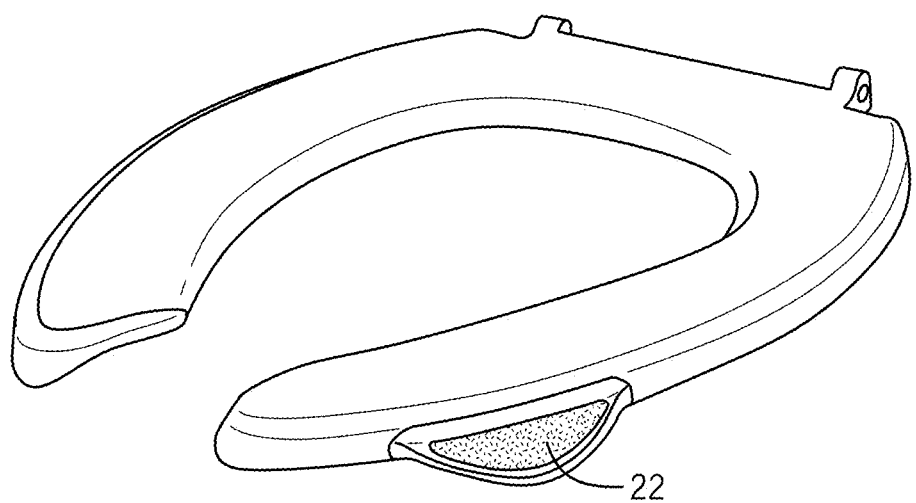
FIG. 4 is a perspective view of a toilet seat comprising a tab according to a second embodiment of the present disclosure.
Figure 5:
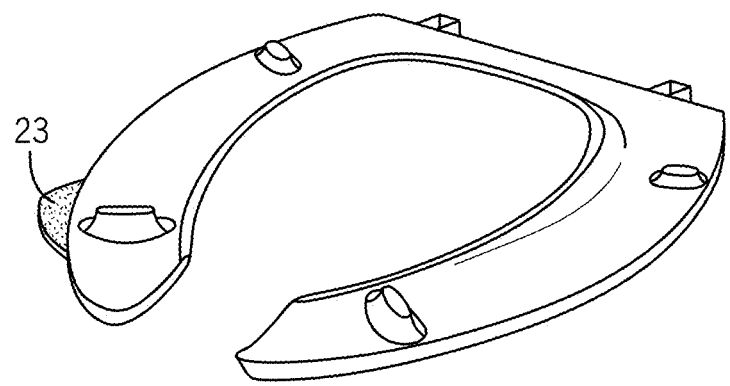
FIG. 5 is a bottom view of the toilet seat comprising the tab according to the second embodiment of the present disclosure.
Figure 6:
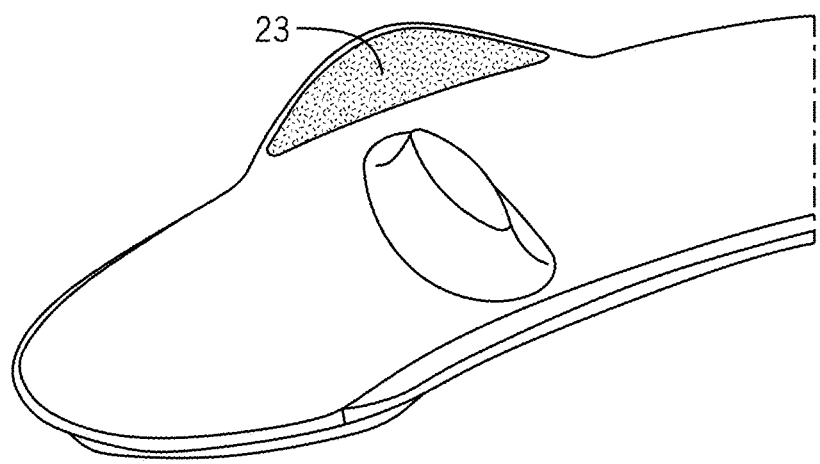
FIG. 6 is an enlarged view of the toilet seat comprising the tab according to the second embodiment of the present disclosure.

FIG. 4 is a perspective view of a toilet seat comprising a tab according to a second embodiment of the present disclosure. FIG. 5 is a bottom view of the toilet seat comprising the tab according to the second embodiment of the present disclosure. FIG. 6 is an enlarged view of the toilet seat comprising the tab according to the second embodiment of the present disclosure.

Referring to FIG. 4 to FIG. 6, the overall configuration of the tab 20 and the toilet seat 10 according to this embodiment is similar to those in the first embodiment. However, the tab 20 according this embodiment is disposed on one side of the rim 11. Also, the copper material is more visible to the toilet user from the appearance of the tab 20. Although FIG. 4 to FIG. 6 show that the toilet seat 10 comprises the gap 12, the toilet seat 10 may also be a closed-front seat without the gap 12 in another embodiment.

In this embodiment, the copper material may be inlaid on an upper surface 22 of the tab 20 and a lower surface 23 of the tab 20. In another embodiment, the tab 20 may have a transparent or translucent case enclosing the inlaid copper material so that the toilet user may tell the copper material from the appearance of the tab 20.

Therefore, the tab 20 according to this embodiment may offer the toilet users an indication that the tab 20 is made from the copper material so that the toilet users can rest assured that the risk of getting infected with the pathogens is low due to the copper material when they use the toilet.

Third Embodiment

Figure 7:
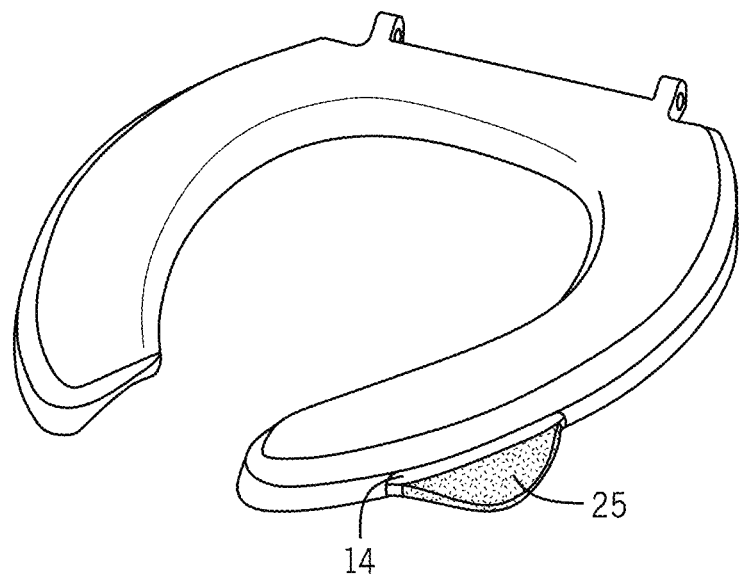
FIG. 7 is a perspective view of a toilet seat comprising a tab according to a third embodiment of the present disclosure.
Figure 8:
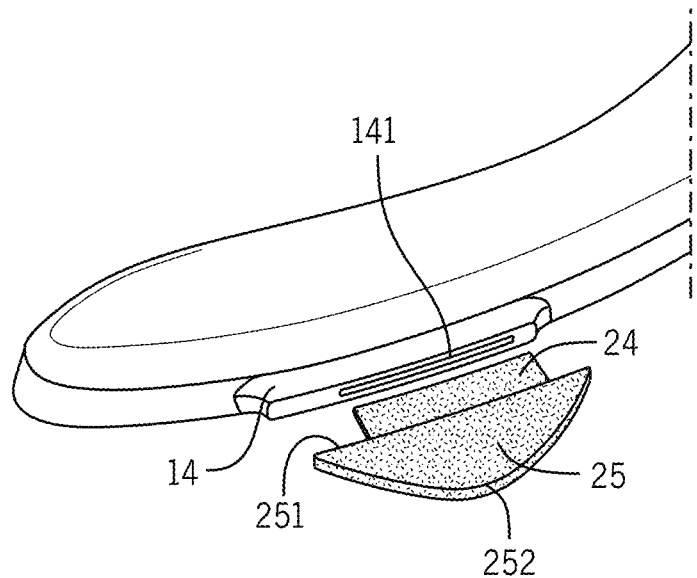
FIG. 8 is an enlarged view of the toilet seat comprising the tab according to the third embodiment of the present disclosure.

FIG. 7 is a perspective view of a toilet seat comprising a tab according to a third embodiment of the present disclosure. FIG. 8 is an enlarged view of the toilet seat comprising the tab according to the third embodiment of the present disclosure.

Referring to FIG. 7 and FIG. 8, the toilet seat 10 comprises a base 14 disposed on one side of the rim 11. The base 14 comprises an elongated groove 141 in communication with an internal space of the base 14. Although FIG. 7 and FIG. 8 show that the toilet seat 10 comprises the gap 12, the toilet seat 10 may also be a closed-front seat without the gap 12 in another embodiment.

Unlike the first embodiment and the second embodiment, the tab 20 according to this embodiment is detachably attached to the toilet seat 10. The tab 20 comprises an insert portion 24 and a grip portion 25 connected to the insert portion 24. The shape and size of the insert portion 24 correspond to the shapes and sizes of the groove 141 and the internal space of the base 14. As illustrated in FIG. 8, the insert portion 24 is in a rectangular shape. Thus, the insert portion 24 may be received in the internal space of the base 14 through the groove 141 when the insert portion 24 of the tab 20 is inserted into the base 14 of the toilet seat 10. The grip portion 25 comprises an elongated rim 251 and a curved rim 252 connected to the elongated rim 251. The elongated rim 251 is longer than the length of the insert portion 24 so that the grip portion 25 is stopped by the elongated rim 251 when the insert portion 24 of the tab 20 is inserted into the base 14 of the toilet seat 10. Thus, the grip portion 25 extends radially outwards from the rim 11 so as to provide a touch point for the toilet users. The tab 20 may be detached from the base 14 of the toilet seat 10 by removing the insert portion 24 of the tab 20 out of the base 14 of the toilet seat 10.

According to this embodiment, like the second embodiment, the toilet users may also tell the copper material from the appearance of the tab 20. In another embodiment, the copper material may be invisible to the toilet user from the appearance of the tab 20. The manufacturing processes are similar to the first embodiment or the second embodiment as discussed earlier. In this embodiment, only the grip portion 25 of the tab 20 or both the grip portion 25 and the insert portion 24 of the tab 20 may be made from the copper material.

In this embodiment, the base 14 of the toilet seat 10 is compatible with any types of the current toilet seats and thus no extra process is required for manufacturing the toilet seat or the toilet lid itself. Also, the tab 20 may be easily removed from the toilet seat 10 when the tab 20 is contaminated by the pathogens, tarnished, or oxidized. The removed tab 20 may be replaced with a new tab 20 regularly when the tab 20 becomes contaminated, tarnished, or oxidized or may be sanitized regularly. Then, the new tab 20 or the sanitized tab 20 may be easily installed on the toilet seat 10. Therefore, these advantages significantly reduce the costs for manufacturing the tab 20 and the toilet seat 10 comprising the tab 20 according to this embodiment. In addition, the tab 20 may further reduce or eliminate the risks for the users to get infected with the pathogens because the tab 20 may be easily removed from and installed on the toilet seat 10 for regular maintenance or replacement.

Fourth Embodiment

Figure 9:
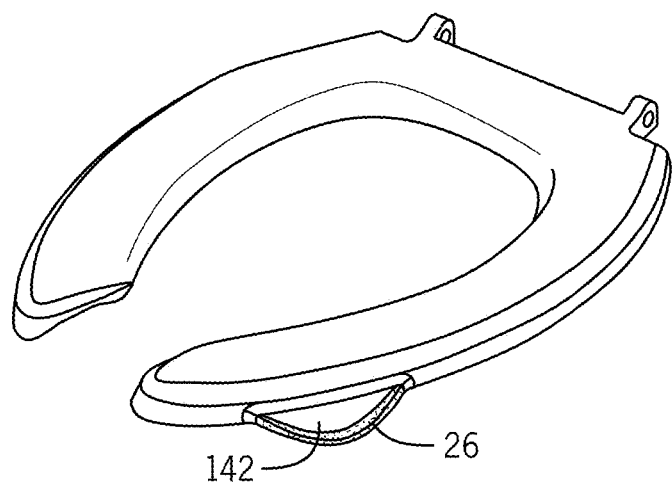
FIG. 9 is a perspective view of a toilet seat comprising a tab according to a fourth embodiment of the present disclosure.
Figure 10:
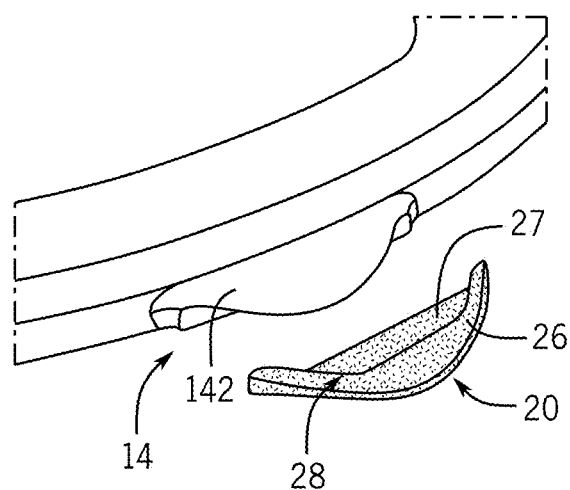
FIG. 10 is an enlarged view of the toilet seat comprising the tab according to the fourth embodiment of the present disclosure.

FIG. 9 is a perspective view of a toilet seat comprising a tab according to a fourth embodiment of the present disclosure. FIG. 10 is an enlarged view of the toilet seat comprising the tab according to the fourth embodiment of the present disclosure.

Referring to FIG. 9 and FIG. 10, like the third embodiment, the tab 20 according to this embodiment is also detachably attached to the toilet seat 10. However, the base 14 of the toilet seat 10 and the tab 20 according to this embodiment have different structures from those in the third embodiment.

Although FIG. 9 and FIG. 10 show that the toilet seat 10 comprises the gap 12, the toilet seat 10 may also be a closed-front seat without the gap 12 in another embodiment. The toilet seat 10 comprises the base 14 disposed on one side of the rim 11. The base 14 comprises a protrusion 142 extending radially outwards from the rim 11. In this embodiment, the protrusion 142 of the base 14 is in a substantially semicircle shape. The protrusion 142 of the base 14 is in any shape and size suitable for a normal human hand size, e.g. having an ergonomic design.

The tab 20 comprises a first surface 26 and a second surface 27 connected to the first surface 26. Thus, the tab 20 forms a curved thin trim. As illustrated in FIG. 10, the first surface 26 is in a substantially C-shaped and the second surface 27 is in a substantially semicircle shape. The second surface 27 is larger in size than the first surface 26 so as to form a groove 28 between the first surface 26 and the second surface 27. The shape and size of the groove 28 correspond to the shape and size of the protrusion 142 of the base 14. Thus, the protrusion 142 of the base 14 may be received in the groove 28 of the tab 20 when the tab 20 is installed on the base 14 of the toilet seat 10. Therefore, the first surface 26 and the second surface 27 of the tab 20 form a touch point for the toilet users. The tab 20 may be detached from the base 14 of the toilet seat 10 by removing the first surface 26 and the second surface 27 of the tab 20 out of the base 14 of the toilet seat 10.

According to this embodiment, like in the second embodiment, the toilet users may also tell the copper material from the appearance of the tab 20. In another embodiment, the copper material may be invisible to the toilet user from the appearance of the tab 20. The manufacturing processes are similar to the first embodiment or the second embodiment as discussed earlier. In this embodiment, only the first surface 26 and the second surface 27 of the tab 20 may be made from the copper material.

In this embodiment, the base 14 of the toilet seat 10 is compatible with any types of the current toilet seats and thus no extra process is required for manufacturing the toilet seat or the toilet lid itself. Also, the tab 20 may be easily removed from the toilet seat 10 when the tab 20 is contaminated by the pathogens, tarnished, or oxidized. The removed tab 20 may be replaced with a new tab 20 regularly when the tab 20 becomes contaminated, tarnished, or oxidized or may be sanitized regularly. Then, the new tab 20 or the sanitized tab 20 may be easily installed on the toilet seat 10. Therefore, these advantages significantly reduce the costs for manufacturing the tab 20 and the toilet seat 10 comprising the tab 20 according to this embodiment. In addition, the tab 20 may further reduce or eliminate the risks for the users to get infected with the pathogens because the tab 20 may be easily removed from and installed on the toilet seat 10 for regular maintenance or replacement.

Fifth Embodiment

Figure 11:
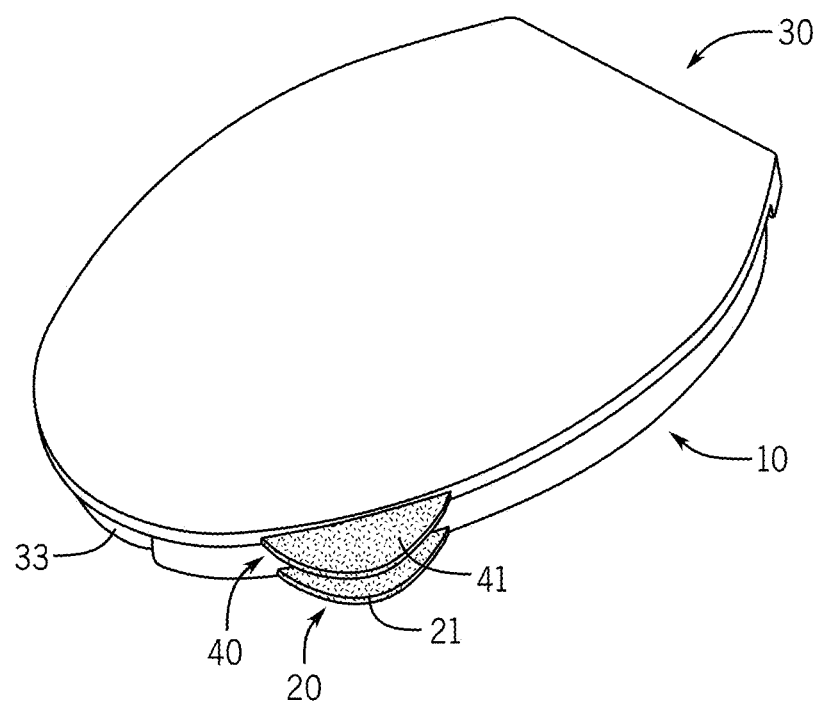
FIG. 11 is a perspective view of a toilet seat comprising a tab and a toilet lid comprising a tab according to a fifth embodiment of the present disclosure.
Figure 12:
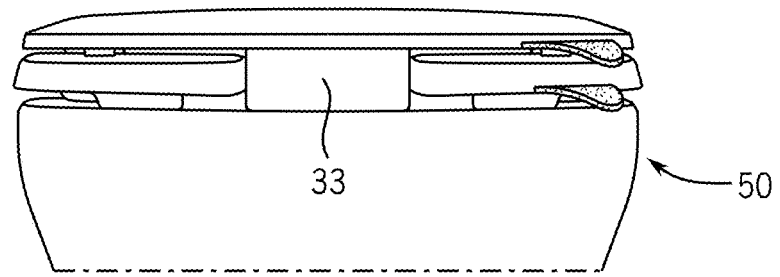
FIG. 12 is a front view of the toilet seat and the toilet lid according to the fifth embodiment of the present disclosure.
Figure 13:
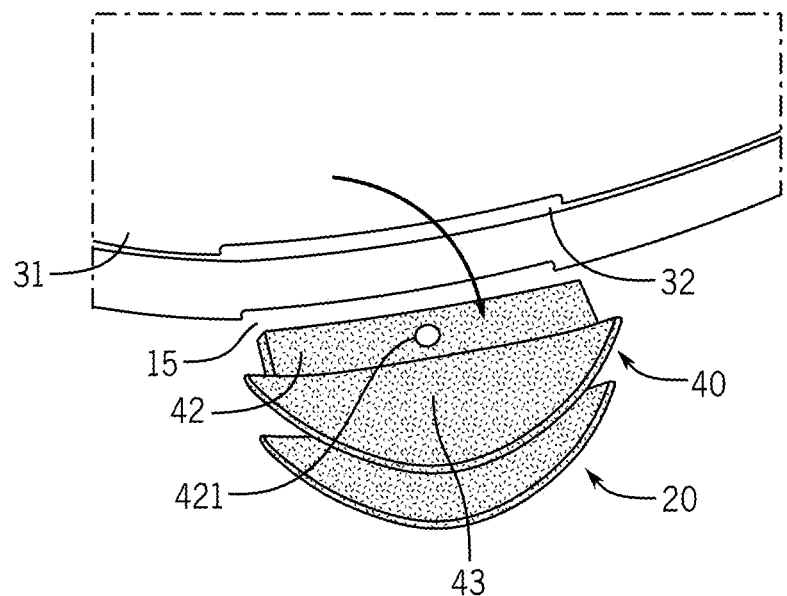
FIG. 13 is an enlarged view of the tabs according to the fifth embodiment of the present disclosure.
Figure 14:
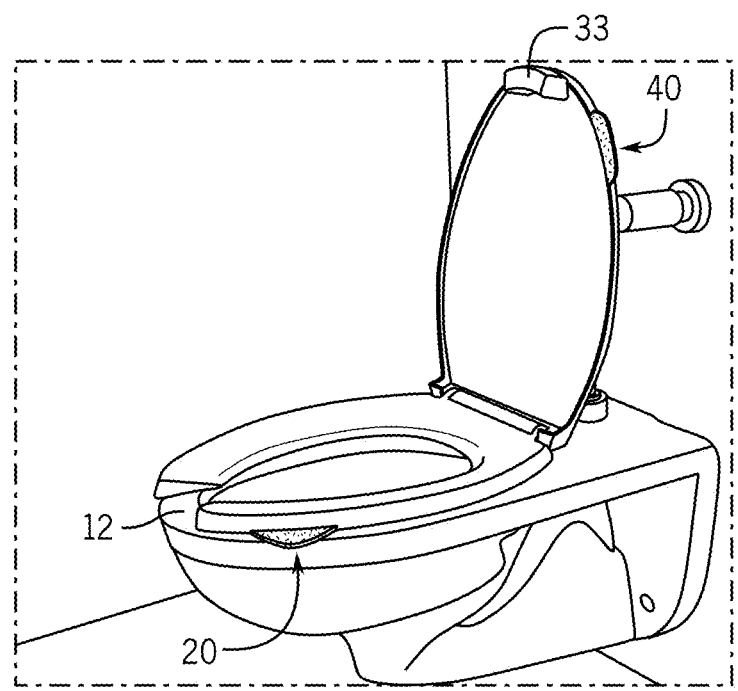
FIG. 14 is a perspective view of the toilet seat and the toilet lid installed on a toilet bowl according to the fifth embodiment of the present disclosure.

FIG. 11 is a perspective view of a toilet seat comprising a tab and a toilet lid comprising a tab according to a fifth embodiment of the present disclosure. FIG. 12 is a front view of the toilet seat and the toilet lid according to the fifth embodiment of the present disclosure. FIG. 13 is an enlarged view of the tabs according to the fifth embodiment of the present disclosure. FIG. 14 is a perspective view of the toilet seat and the toilet lid installed on a toilet bowl according to the fifth embodiment of the present disclosure.

Referring to FIG. 11 to FIG. 14, a toilet comprises a toilet bowl 50, a toilet seat 10 pivotably connected to the toilet bowl 50, and a toilet lid 30 pivotably connected to the toilet seat 10 and/or the toilet bowl 50.

The toilet seat 10 comprises a U-shaped rim 11 having a gap 12 disposed at a front end of a rim 11. The front end of the rim 11 is defined by an end facing a toilet user. The gap 12 in the toilet seat 10 leaves a space between the toilet lid 30 and the toilet bowl 50. The toilet seat 10 further comprises a tab 20 detachably attached to the rim 11 of the toilet seat 10 and an elongated groove 15 disposed on and extended along the rim 11 of the toilet seat 10. Thus, the groove 15 forms an internal space configured to receive the tab 20.

Like in the third embodiment, the tab 20 according to this embodiment is detachably attached to the toilet seat 10 and has a structure similar to the tab 20 in the third embodiment (also referring to FIG. 8). However, the tab 20 according to this embodiment further comprises a screw hole disposed on the insert portion 24 and configured to receive a screw. The screw is configured to securely attach the tab 20 to the rim 11 of the toilet seat 10 when the insert portion 24 is received in the internal space formed by the groove 15.

Like toilet seats, toilet lids are easily contaminated by the pathogens due to the toilet flushing. Thus, a tab 40 may be detachably attached to the toilet lid 30 according to this embodiment so as to achieve the advantages as discussed above. The toilet lid 30 comprises an elongated groove 32 disposed on and extended along a rim 31 of the toilet lid 30. Thus, the groove 32 forms an internal space configured to receive the tab 40. The groove 32 of the toilet lid 30 is substantially aligned with and disposed above the groove 15 of the toilet seat 10 when the toilet lid 30 and the toilet seat 10 are in the closed status.

The tab 40 has the same structure as the tab 20 according to this embodiment. Specifically, the tab 40 comprises a curved rim 41, an insert portion 42, and a grip portion 43 connected to the insert portion 42. The grip portion 43 comprises the curved rim 41 and thus is in a substantially semicircle shape. The tab 40 may be in any shape and size suitable for a normal human hand size, e.g. having an ergonomic design. The tab 40 further comprises a screw hole 421 disposed on the insert portion 42 and configured to receive a screw. The screw is configured to securely attach the tab 40 to the rim 31 of the toilet lid 30 when the insert portion 42 is received in the internal space formed by the groove 32.

When both the insert portions 24, 42 are respectively inserted into the grooves 15, 32 and the toilet seat 10 and the toilet lid 30 are in the closed status, the tabs 20, 40 are substantially aligned and spaced apart with each other so as to have a simple and clean appearance of the toilet. The tabs 20, 40 may have substantially the same dimensions and shapes. The grip portion 25 of the tab 20 and the grip portion 43 of the tab 40 may be spaced apart at any distance, e.g. 23 mm, so that the fingers of the users may access the space to open the toilet seat 10 and the toilet lid 30.

The tabs 20, 40 may be made from the copper material. The copper material may be either visible or invisible to the toilet users from the appearance of the tabs 20, 40. The manufacturing processes are similar to the first embodiment or the second embodiment as discussed earlier. However, the antibacterial material is not limited to the copper. In another embodiment, any other antibacterial material may be used.

This embodiment provides at least two touch points for the toilet users. Also, the tabs 20, 40 may be easily removed from and installed on the toilet seat 10 and the toilet lid 30 for regular maintenance or replacement. Thus, the contaminated, tarnished, or oxidized tabs 20, 40 may be replaced easily with new tabs or sanitized easily with toilet cleaning agents, e.g. nitric acid. Therefore, the tabs 20, 40 may further reduce or eliminate the risks for the toilet users to get infected with the pathogens when opening or closing the toilet seat 10 or the toilet lid 30. The toilet seat 10, the toilet lid 30, and the tabs 20, 40 have simple structures and thus this reduces the manufacturing costs.

As discussed above, the gap 12 in the toilet seat 10 leaves a space between the toilet lid 30 and the toilet bowl 50. Thus, in a current toilet in the art, the excrement particles containing the pathogens may escape from the space and spread in the form of the aerosols even when the toilet lid is in the closed status. Therefore, the current toilet in the art increases the risks for the users to get infected with the pathogens when the toilet is flushed.

According to this embodiment, the toilet lid 30 comprises a front seal 33 disposed at the front end of the rim 31 and at a position corresponding to the gap 12 of the toilet seat 10. The front seal 33 extends in a substantially vertical direction relative to a surface forming by the toilet lid 30. The front seal 33 has a width equal to or smaller than a width of the gap 12. The front seal 33 has a height corresponding to the distance between the toilet lid 30 and the toilet bowl 50. The front seal 33 may be made from a hard-rubberized material. In another embodiment, the front seal 33 may be made from the copper material. Therefore, the front seal 33 may become a third touch point for the toilet users. The copper material may be either visible or invisible to the toilet users from the appearance of the front seal 33. The manufacturing processes are similar to the first embodiment or the second embodiment as discussed earlier.

When the toilet lid 30 is in the closed status, the front seal 33 may be received in the gap 12 and thus may function as a shield configured to prevent the pathogens from escaping from the space between the toilet lid 30 and the toilet bowl 50 caused by the gap 12 of the toilet seat 10. Therefore, the risks for the users to get infected with the pathogens when the toilet is flushed may be further reduced.

Sixth Embodiment

Figure 15:
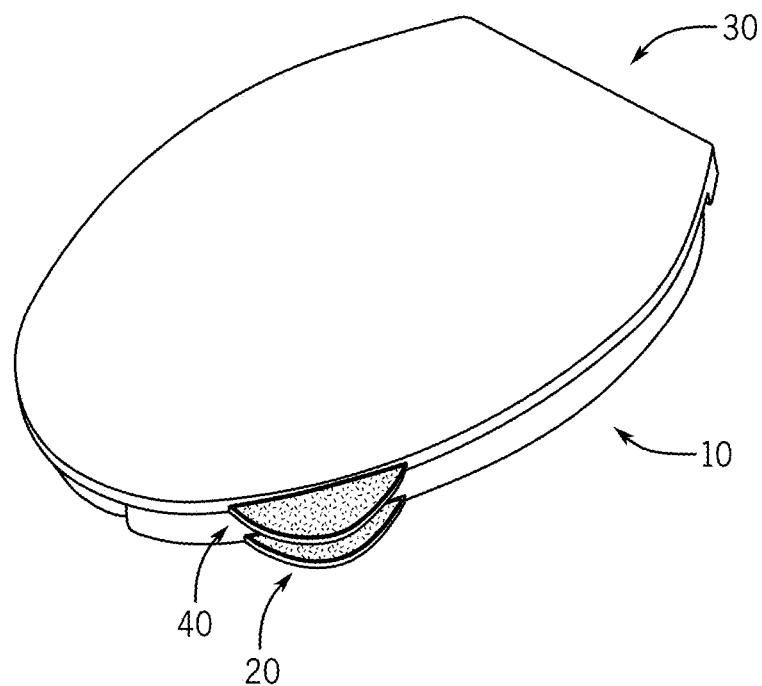
FIG. 15 is a perspective view of a toilet seat comprising a tab and a toilet lid comprising a tab according to a sixth embodiment of the present disclosure.
Figure 16:
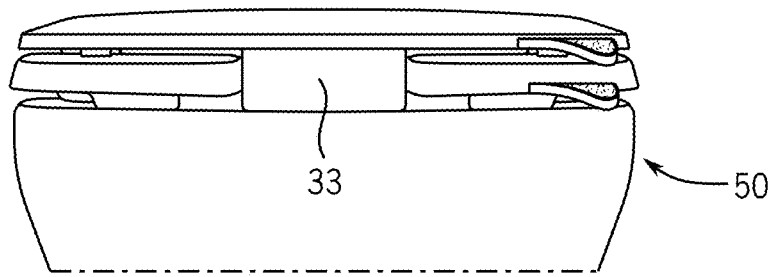
FIG. 16 is a front view of the toilet seat and the toilet lid according to the sixth embodiment of the present disclosure.
Figure 17:
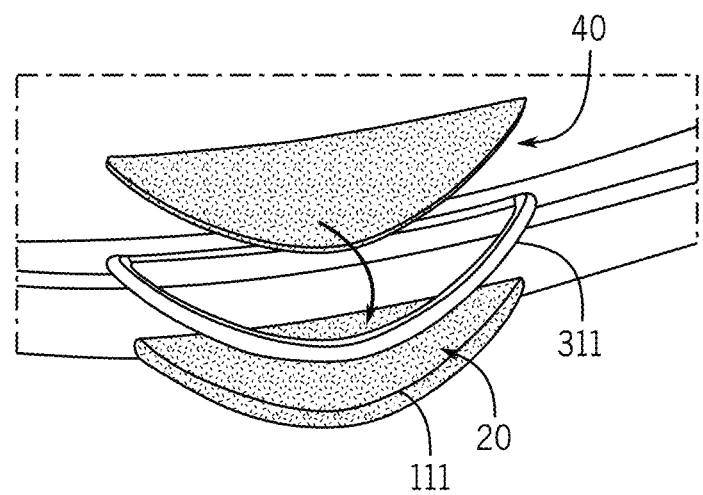
FIG. 17 is an enlarged view of the tabs according to the sixth embodiment of the present disclosure.
Figure 18:
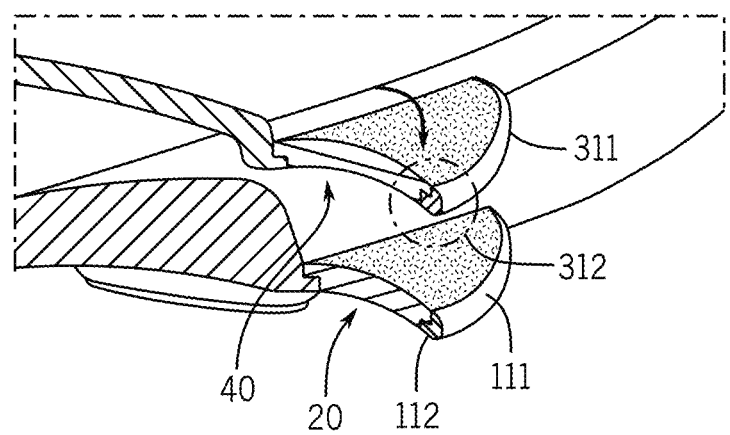
FIG. 18 is a cross-sectioned view of the tabs according to the sixth embodiment of the present disclosure.

FIG. 15 is a perspective view of a toilet seat comprising a tab and a toilet lid comprising a tab according to a sixth embodiment of the present disclosure. FIG. 16 is a front view of the toilet seat and the toilet lid according to the sixth embodiment of the present disclosure. FIG. 17 is an enlarged view of the tabs according to the sixth embodiment of the present disclosure. FIG. 18 is a cross-sectioned view of the tabs according to the sixth embodiment of the present disclosure.

Referring to FIG. 15 to FIG. 18, the overall configuration of the tabs 20, 40, the toilet seat 10, the toilet lid 30, and the toilet bowl 50 according to this embodiment is similar to those in the fifth embodiment. However, instead of the grooves 15, 32, the rim 11 of the toilet seat 10 comprises a frame 111 extending radially outwards from the rim 11 and the rim 31 of the toilet lid 30 comprises a frame 311 extending radially outwards from the rim 31. As shown in FIG. 18, the frame 111 has an L-shaped cross-section 112 configured to receive the tab 20 and the frame 311 has an L-shaped cross-section 312 configured to receive the tab 40. In this embodiment, the frames 111, 311 are in a substantially semicircle shape and may be in any shape and size suitable for a normal human hand size, e.g. having an ergonomic design. The frame 311 of the toilet lid 30 is substantially aligned with and disposed above the frame 111 of the toilet seat 10 when the toilet lid 30 and the toilet seat 10 are in the closed status.

The tab 40 has the same structure as the tab 20 according to this embodiment. Specifically, the tabs 20, 40 respectively comprise a curved rim 21 and a curved rim 41. As shown in FIG. 18, the curved rim 21 has a reverse L-shaped cross-section 211 corresponding to the L-shaped cross-section 112 of the frame 111. The curved rim 41 has a reverse L-shaped cross-section 411 corresponding to the L-shaped cross-section 312 of the frame 311. Thus, the tabs 20, 40 may be respectively received in the frames 111, 311.

When both the tabs 20, 40 are respectively received in the frames 111, 311 and the toilet seat 10 and the toilet lid 30 are in the closed status, the tabs 20, 40 are substantially aligned and spaced apart with each other so as to have a simple and clean appearance of the toilet. The tabs 20, 40 may have substantially the same dimensions and shapes. The tabs 20, 40 may be spaced apart at any distance, e.g. 23 mm, so that the fingers of the users may access the space to open the toilet seat 10 and the toilet lid 30.

The tabs 20, 40 may be made from the copper material. The copper material may be either visible or invisible to the toilet users from the appearance of the tabs 20, 40. The manufacturing processes are similar to the first embodiment or the second embodiment as discussed earlier. However, the antibacterial material is not limited to the copper. In another embodiment, any other antibacterial material may be used.

This embodiment provides two touch points for the toilet users. Also, the tabs 20, 40 may be easily removed from and received in the toilet seat 10 for regular maintenance or replacement. Thus, the contaminated, tarnished, or oxidized tabs 20, 40 may be replaced easily with new tabs or sanitized easily with toilet cleaning agents, e.g. nitric acid. Therefore, the tabs 20, 40 may further reduce or eliminate the risks for the toilet users to get infected with the pathogens when opening or closing the toilet seat 10 or the toilet lid 30.

Seventh Embodiment

Figure 19:
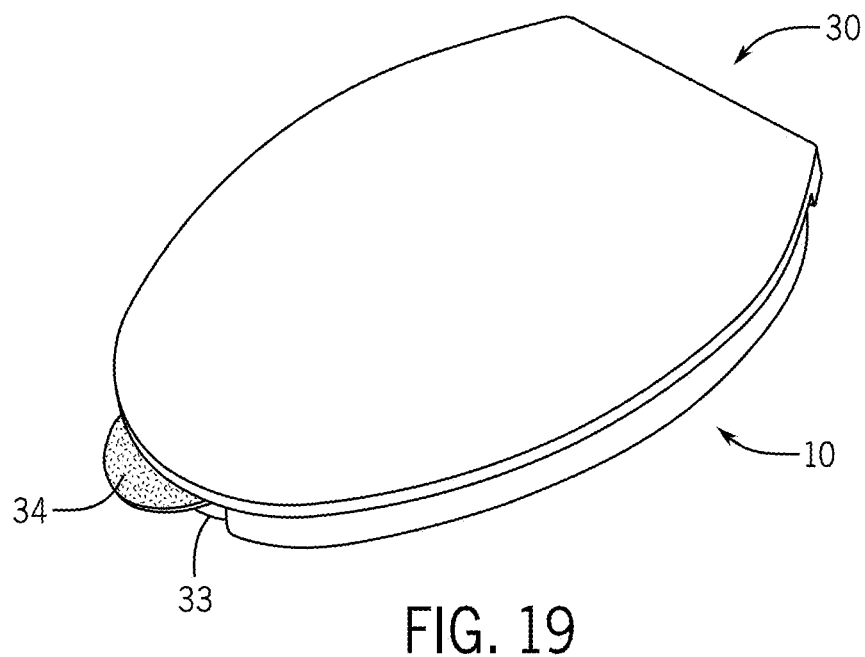
FIG. 19 is a perspective view of a front seal and a front tab according to a seventh embodiment of the present disclosure.
Figure 20:
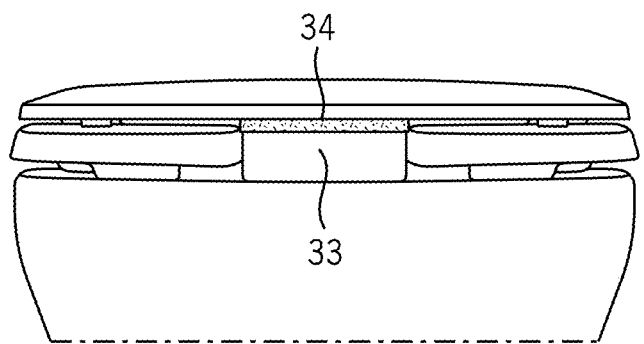
FIG. 20 is a front view of the front seal and the front tab according to the seventh embodiment of the present disclosure.
Figure 21:
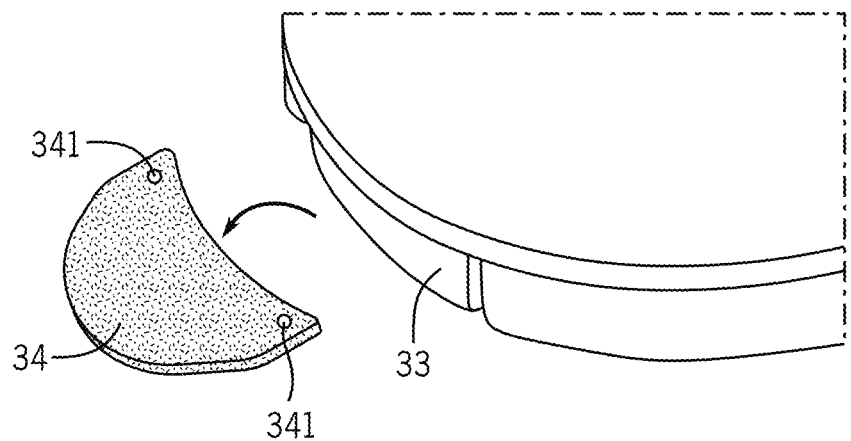
FIG. 21 is an enlarged view of the front seal and the front tab according to the seventh embodiment of the present disclosure.
Figure 22:
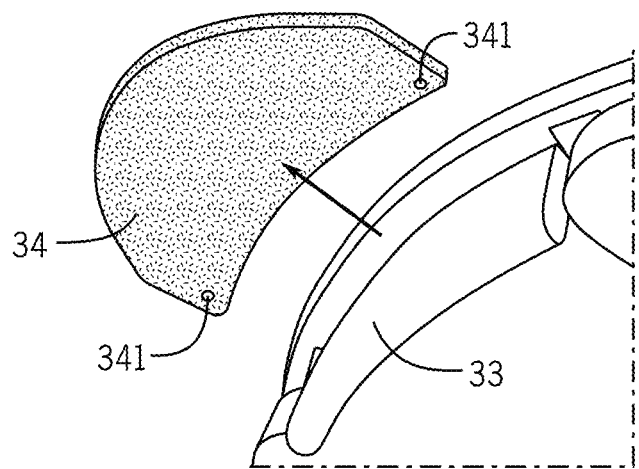
FIG. 22 is a bottom view of the front seal and the front tab according to the seventh embodiment of the present disclosure.
Figure 23:
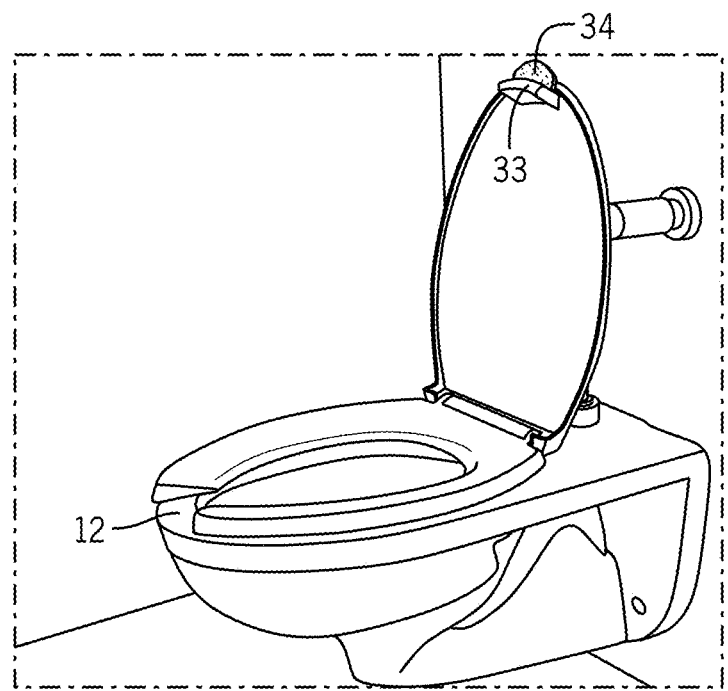
FIG. 23 is a perspective view illustrating that the front tab is attached to the front seal according to the seventh embodiment of the present disclosure.

FIG. 19 is a perspective view of a front seal and a front tab according to a seventh embodiment of the present disclosure. FIG. 20 is a front view of the front seal and the front tab according to the seventh embodiment of the present disclosure. FIG. 21 is an enlarged view of the front seal and the front tab according to the seventh embodiment of the present disclosure. FIG. 22 is a bottom view of the front seal and the front tab according to the seventh embodiment of the present disclosure. FIG. 23 is a perspective view illustrating that the front tab is attached to the front seal according to the seventh embodiment of the present disclosure.

Referring to FIG. 19 to FIG. 23, the toilet lid 30 according to this embodiment comprises the same front seal 33 as in the fifth embodiment. However, the toilet lid 30 further comprises a front tab 34 configured to be attached to the front seal 33. The front tab 34 comprises screw holes 341 configured to receive screws so that the front tab 34 can be securely attached to the front seal 33.

When the front tab 34 is attached to the front seal 33, the front tab 34 is disposed on the toilet lid 30 at the front end of the rim 11 and above the gap 12 of the toilet seat 10 and extends forwards from the rim 11 in a substantially horizontal direction. In this embodiment, the front tab 34 in a substantially semicircle shape and has a width equal to or smaller than the width of the gap 12. The tab 20 may have a length suitable for a normal human hand size, e.g. having an ergonomic design.

According to this embodiment, the front tab 34 is made from the copper material. The copper material may be either visible or invisible to the toilet users from the appearance of the front tab 34. The manufacturing processes are similar to the first embodiment or the second embodiment as discussed earlier.

In another embodiment, the tab 20 and/or the tab 40 as described in any other embodiments may be added to the toilet.

Therefore, the risks for the users to get infected with the pathogens when the toilet is flushed may be reduced because the front tab 34 may function as a touch point for the toilet users to open or close the toilet lid 30.

Eighth Embodiment

Figure 24:
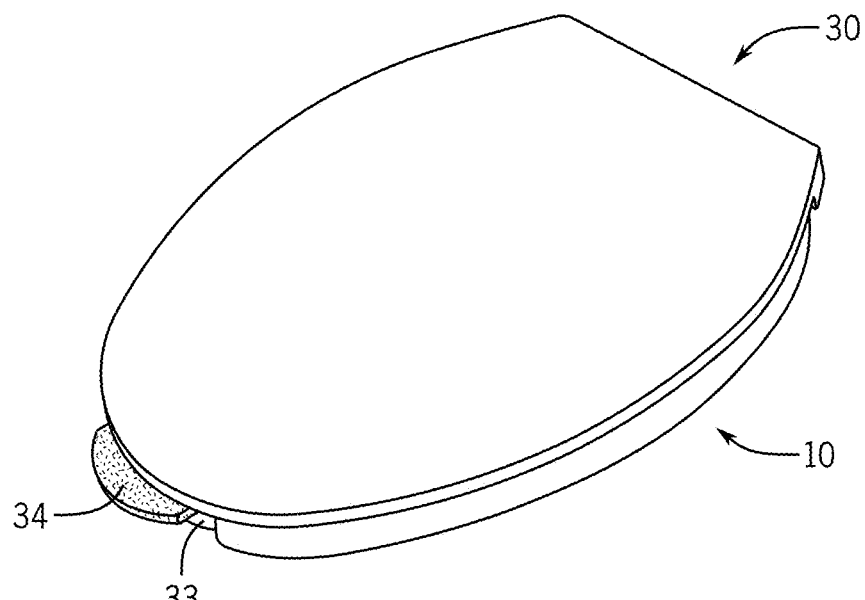
FIG. 24 is a perspective view of a front seal and a front tab according to an eighth embodiment of the present disclosure.
Figure 25:
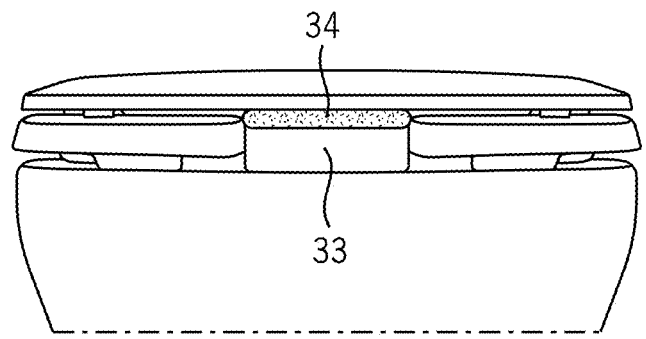
FIG. 25 is a front view of the front seal and the front tab according to the eighth embodiment of the present disclosure.
Figure 26:
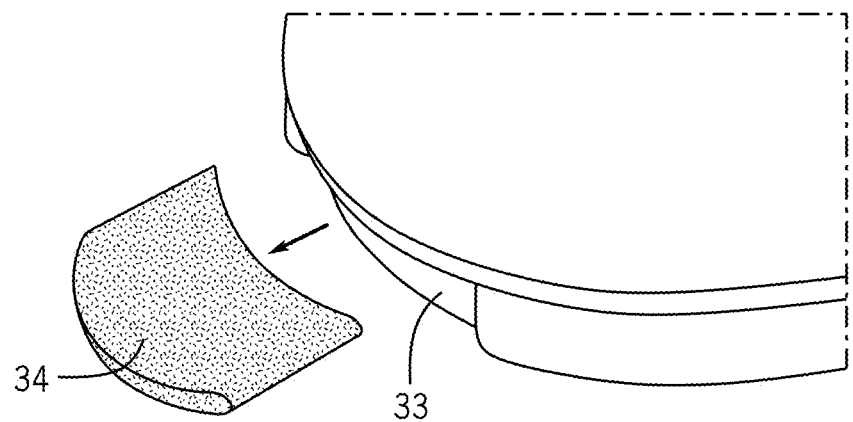
FIG. 26 is an enlarged view of the front seal and the front tab according to the eighth embodiment of the present disclosure.
Figure 27:
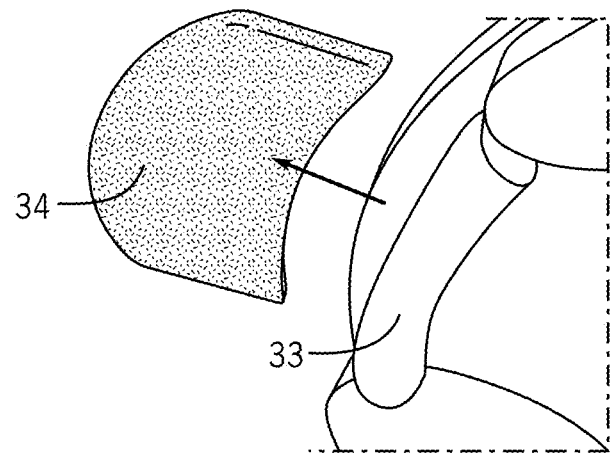
FIG. 27 is a bottom view of the front seal and the front tab according to the eighth embodiment of the present disclosure.
Figure 28:
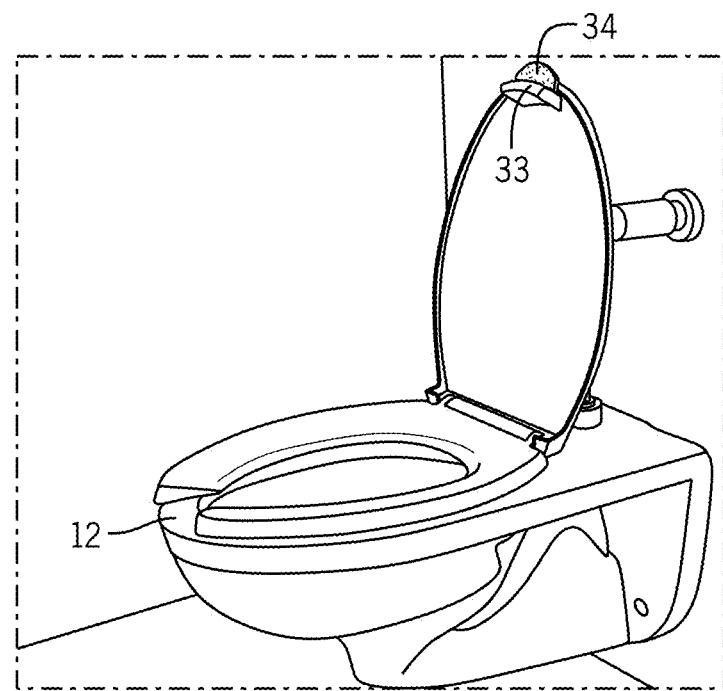
FIG. 28 is a perspective view illustrating that the front tab is connected to the front seal according to the eighth embodiment of the present disclosure.

FIG. 24 is a perspective view of a front seal and a front tab according to an eighth embodiment of the present disclosure. FIG. 25 is a front view of the front seal and the front tab according to the eighth embodiment of the present disclosure. FIG. 26 is an enlarged view of the front seal and the front tab according to the eighth embodiment of the present disclosure. FIG. 27 is a bottom view of the front seal and the front tab according to the eighth embodiment of the present disclosure. FIG. 28 is a perspective view illustrating that the front tab is connected to the front seal according to the eighth embodiment of the present disclosure.

Referring to FIG. 24 to FIG. 28, the overall configuration of the front seal 33 and the front tab 34 according to this embodiment is similar to those in the seventh embodiment. However, the front tab 34 according to this embodiment is thicker than that in the seventh embodiment. Therefore, the front tab 34 can offer a firmer grip when the toilet users lift up or drop down the toilet lid 30.

Ninth Embodiment

Figure 29:
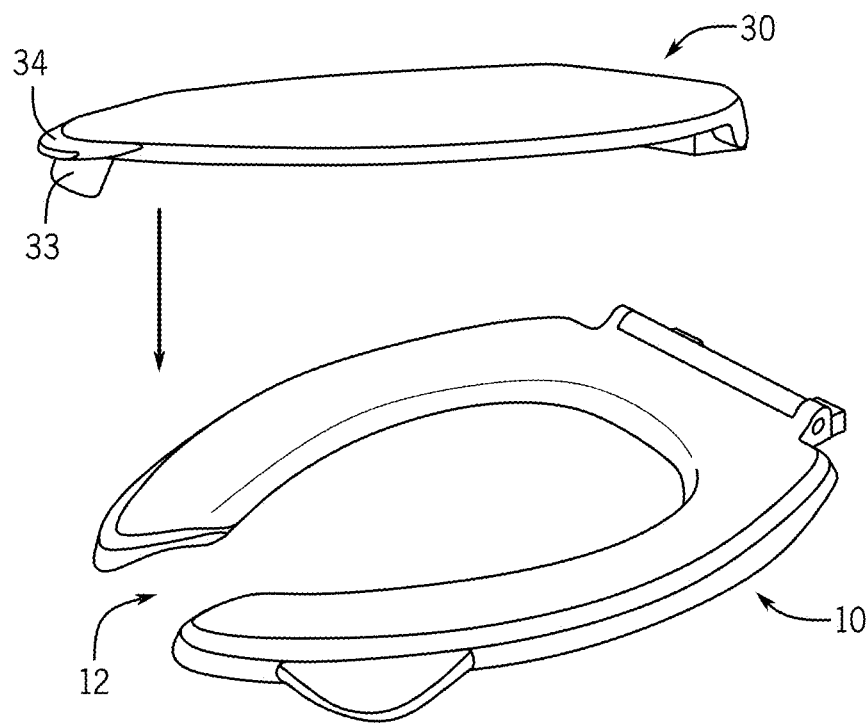
FIG. 29 is an explosive view of a toilet lid comprising a front seal and a front tab according to a ninth embodiment of the present disclosure.
Figure 30:
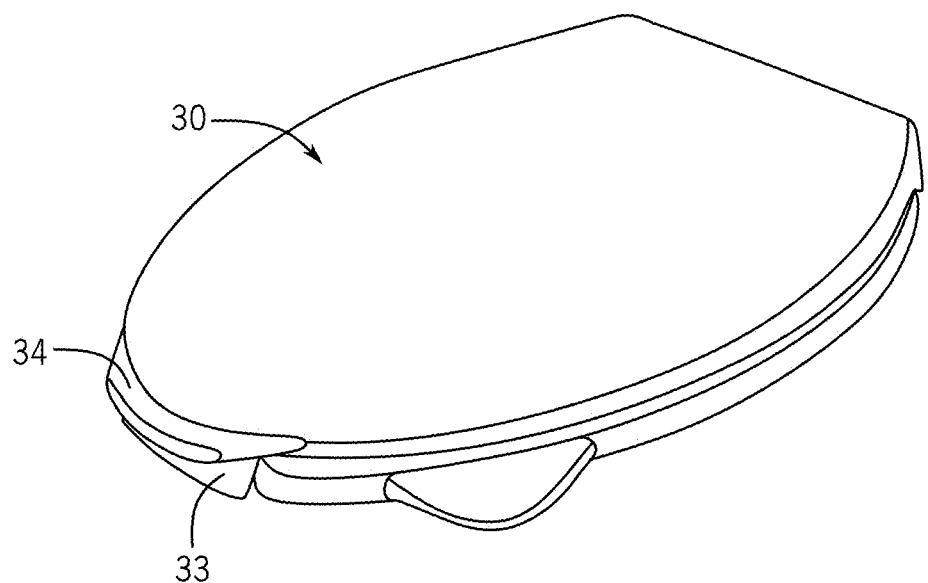
FIG. 30 is a perspective view of the toilet lid comprising the front seal and the front tab according to the ninth embodiment of the present disclosure.

FIG. 29 is an explosive view of a toilet lid comprising a front seal and a front tab according to a ninth embodiment of the present disclosure. FIG. 30 is a perspective view of the toilet lid comprising the front seal and the front tab according to the ninth embodiment of the present disclosure.

Referring to FIG. 29 and FIG. 30, the overall configuration of the front seal 33 and the front tab 34 according to this embodiment is similar to those in the seventh embodiment and the eighth embodiment. However, the front seal 33 tilts down slightly to substantially cover the space between the toilet lid 30 and the toilet bowl caused by the gap 12 of the toilet seat 10.

Therefore, the front seal 33 may function as a shield configured to prevent the pathogens from escaping from the space between the toilet lid 30 and the toilet bowl caused by the gap 12 of the toilet seat 10. Thus, the risks for the toilet users to get infected with the pathogens may be further reduced when the toilet is flushed.

Tenth Embodiment

Figure 31:
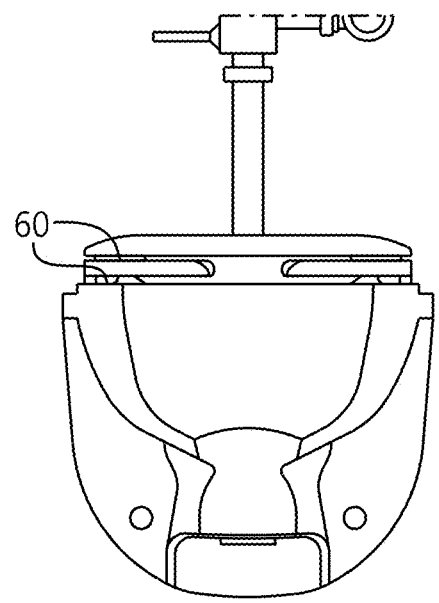
FIG. 31 is a front view illustrating the gaps between a current toilet bowl and a current toilet seat and between the current toilet seat and a current toilet lid in the art.
Figure 32:
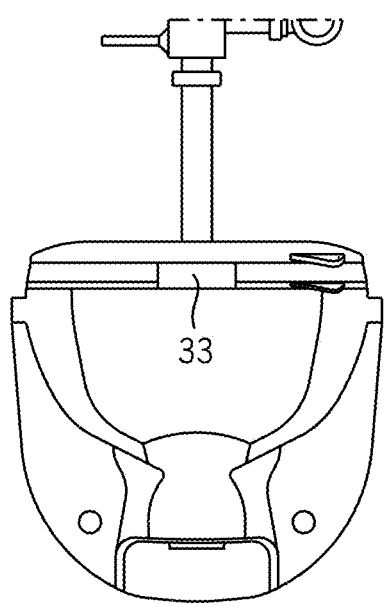
FIG. 32 is a front view illustrating the gaps between a toilet bowl and a toilet seat and between the toilet seat and a toilet lid according to a tenth embodiment of the present disclosure.
Figure 33:
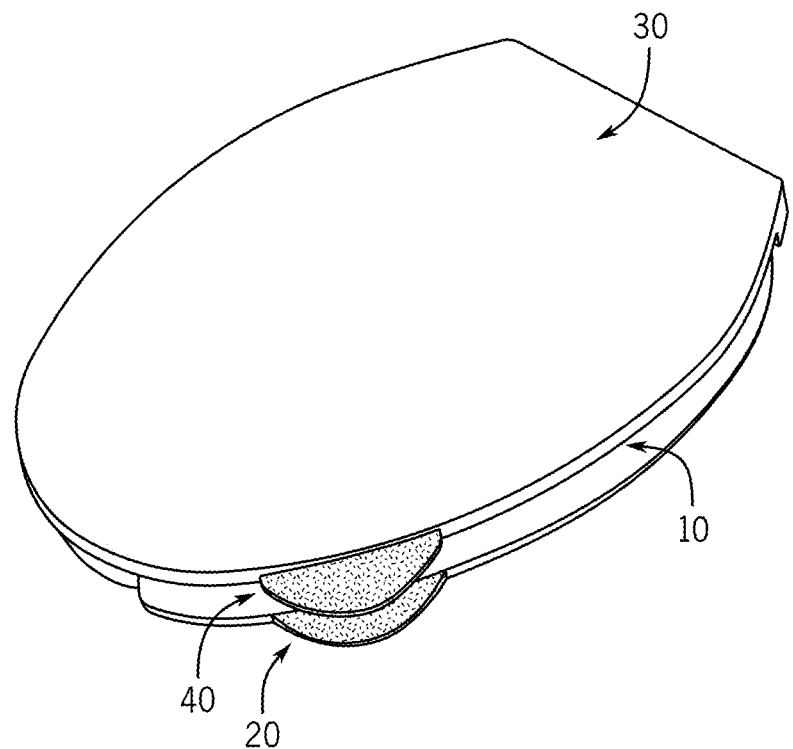
FIG. 33 is a perspective view of a toilet seat comprising a tab and a toilet lid comprising a tab according to the tenth embodiment of the present disclosure.
Figure 34:
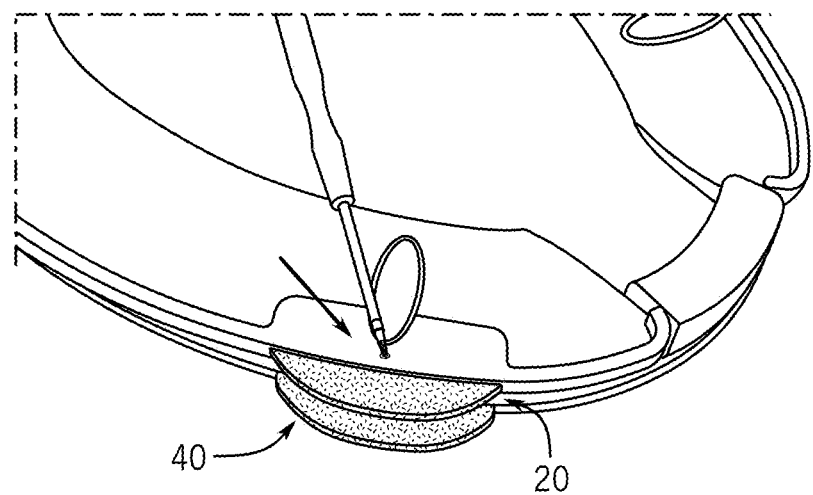
FIG. 34 is a bottom view of the toilet seat and the toilet lid, illustrating the installation of the toilet seat and the toilet lid according to the tenth embodiment of the present disclosure.
Figure 35:
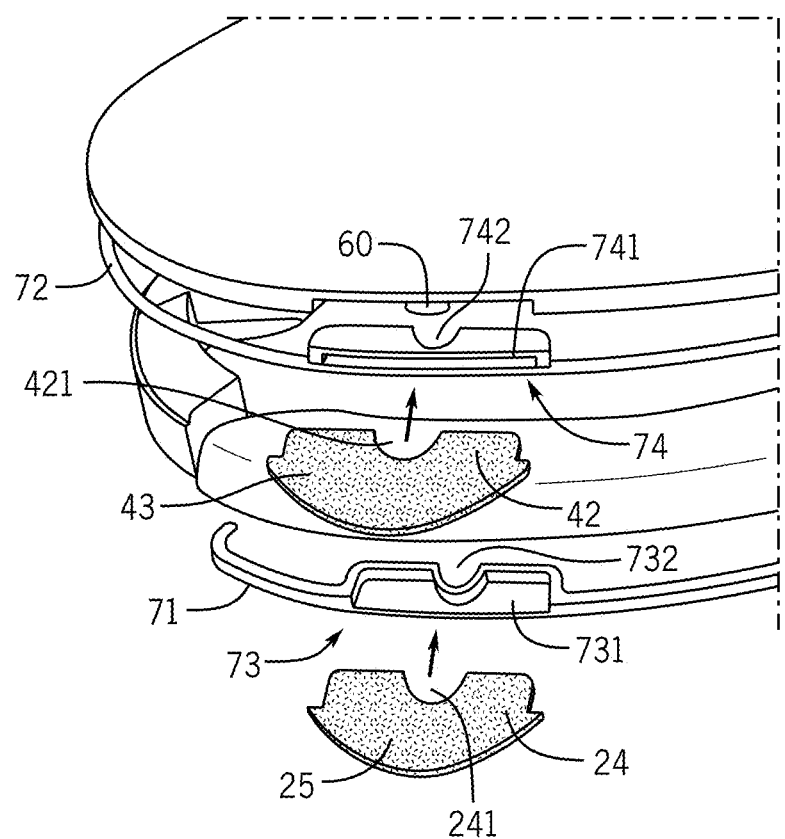
FIG. 35 is an explosive view of the toilet seat and the toilet lid according to the tenth embodiment of the present disclosure.
Figure 38:
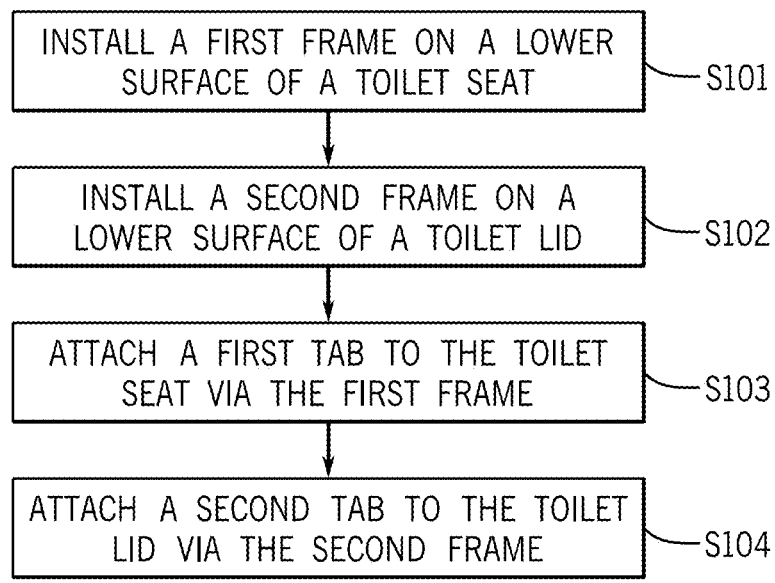
FIG. 38 is a flow chart illustrating a method for assembling the toilet seat and the toilet lid.

FIG. 31 is a front view illustrating the gaps between a current toilet bowl and a current toilet seat and between the current toilet seat and a current toilet lid in the art. FIG. 32 is a front view illustrating the gaps between a toilet bowl and a toilet seat and between the toilet seat and a toilet lid according to a tenth embodiment of the present disclosure. FIG. 33 is a perspective view of a toilet seat comprising a tab and a toilet lid comprising a tab according to the tenth embodiment of the present disclosure. FIG. 34 is a bottom view of the toilet seat and the toilet lid, illustrating the installation of the toilet seat and the toilet lid according to the tenth embodiment of the present disclosure. FIG. 35 is an explosive view of the toilet seat and the toilet lid according to the tenth embodiment of the present disclosure. FIG. 38 is a flow chart illustrating a method for assembling the toilet seat and the toilet lid.

Referring to FIG. 31, the current toilet seat and the current toilet lid in the art comprise a plurality of protrusions 60 disposed on the lower surfaces thereof. Thus, there is a gap of about 8 mm between a current toilet bowl and the current toilet seat and there is a gap of about 3 mm between the current toilet seat and the current toilet lid. Thus, in the current toilet, the excrement particles containing the pathogens may escape from the gaps and spread in the form of the aerosols even when the toilet seat and the toilet lid are in the closed status. Therefore, these gaps increase the risks for the users to get infected with the pathogen when the toilet is flushed.

Referring to FIG. 32 to FIG. 35, like in the fifth embodiment and the sixth embodiment, this embodiment offers two touch points for the toilet users by providing a tab 20 detachably attached to the toilet seat 10 and a tab 40 detachably attached to the toilet lid 30. However, the toilet according to this embodiment further comprises a first frame 71 and a second frame 72. The first frame 71 is disposed between the toilet bowl 50 and the toilet seat 10 and the second frame 72 is disposed between the toilet seat 10 and the toilet lid 30. The first frame 71 and the second frame 72 have thicknesses corresponding to the heights of protrusions 60 so that the first frame 71 and the second frame 72 can fill the gaps between the toilet bowl 50 and the toilet seat 10 and between the toilet seat 10 and the toilet lid 30.

The first frame 71 comprises a base 73 and the second frame 72 comprises a base 74. The base 73 comprises a groove 731 configured to receive the tab 20 and a hole 732 configured to receive the protrusion 60. The base 74 comprises a groove 741 configured to receive the tab 40 and a hole 742 configured to receive the protrusion 60. The shapes and sizes of the holes 732, 742 correspond to the shapes and sizes of the protrusions 60. The first frame 71 and the second frame 72 may have substantially the same dimensions and shapes.

The tab 20 comprises an insert portion 24 and a grip portion 25 connected to the insert portion 24. The shape and size of the insert portion 24 correspond to the shape and size of the groove 731. The tab 40 comprises an insert portion 42 and a grip portion 43 connected to the insert portion 42. The shape and size of the insert portion 42 correspond to the shape and size of the groove 741. The insert portion 24 comprises a hole 241 configured to receive the protrusion 60 and the insert portion 42 comprises a hole 421 configured to receive the protrusion 60. The shapes and sizes of the holes 241, 421 correspond to the shapes and sizes of the protrusions 60. The tabs 20, 40 may have substantially the same dimensions and shapes.

When assembling the toilet, the tabs 20, 40 are respectively inserted into and securely attached to the grooves 731, 741 via screws. The protrusions 60 are inserted into the holes 732, 742, 241, 421. The first frame 71 is sandwiched between the toilet bowl 50 and the toilet seat 10 and the second frame 72 is sandwiched between the toilet seat 10 and the toilet lid 30.

The tabs 20, 40 may be made from the copper material. The copper material may be either visible or invisible to the toilet users from the appearance of the tabs 20, 40. The manufacturing processes are similar to the first embodiment or the second embodiment as discussed earlier. However, the antibacterial material is not limited to the copper. In another embodiment, any other antibacterial material may be used.

This embodiment provides two touch points for the toilet users. Also, the tabs 20, 40 may be easily removed from and received in the toilet seat 10 for regular maintenance or replacement. Thus, the contaminated, tarnished, or oxidized tabs 20, 40 may be replaced easily with new tabs or sanitized easily with toilet cleaning agents, e.g. nitric acid. Therefore, the tabs 20, 40 may further reduce or eliminate the risks for the toilet users to get infected with the pathogens when opening or closing the toilet seat 10 or the toilet lid 30. The first frame 71 and the second frame 72 may function as seals configured to prevent the pathogens from escaping from the gaps between the toilet bowl 50 and the toilet seat 10 and between the toilet seat 10 and the toilet lid 30. Therefore, the risks for the toilet users to get infected with the pathogens may be further reduced when the toilet is flushed.

FIG. 38 illustrates a method for assembling the toilet seat and the toilet lid according to one or more embodiments of the present disclosure.

At act S101, the toilet user may install the first frame 71 on the lower surface of the toilet seat 10. Specifically, the toilet user may align the hole 732 of the base 73 and the protrusion 60 disposed on the lower surface of the toilet seat 10 so that the protrusion 60 may be disposed in the hole 732 of the base 73. Thus, the first frame 71 is disposed between the toilet bowl 50 and the toilet seat 10 and seals a first gap between the toilet bowl 50 and the toilet seat 10 when the toilet seat 10 is in a closed position with respect to the toilet bowl 50.

At act S102, the toilet user may install the second frame 72 on the lower surface of the toilet lid 30. Specifically, the toilet user may align the hole 742 of the base 74 and the protrusion 60 disposed on the lower surface of the toilet lid 30 so that the protrusion 60 may be disposed in the hole 742 of the base 74. Thus, the second frame 72 is disposed between the toilet seat 10 and the toilet lid 30 and seals a second gap between the toilet seat 10 and the toilet lid 30 when the toilet lid 30 is in a closed position with respect to the toilet seat 10.

At act S103, the toilet user may attach the tab 20 to the toilet seat 10 via the first frame 71. Specifically, the insert portion 24 of the tab 20 may be inserted into and received in the groove 731 of the first frame 71. The grip portion 25 of the tab 20 extends radially outwards from the first frame 71 so as to provide a first touch point for the toilet user when the insert portion 24 of the tab 20 is inserted into the groove 731 of the first frame 71. The copper tab sheet may be inmolded to form the tab 20 on the lower surface 13 of the toilet seat 10.

In some examples, act S104 is optionally included. At act S104, the toilet user may attach the tab 40 to the toilet lid 30 via the second frame 72. Specifically, the insert portion 42 of the tab 40 may be inserted into and received in the groove 741 of the second frame 72. The grip portion 43 of the tab 40 extends radially outwards from the second frame 72 so as to provide a second touch point for the toilet users when the insert portion 42 of the tab 40 is inserted into the groove 741 of the second frame 72.

In another embodiment, a different sequence of the above discussed acts may be used in the method. For example, act S103 and act S104 may be performed before act S101 and act S102. For another example, act S102 may be performed before act S101; act S104 may be performed before act S103.

Eleventh Embodiment

Figure 36:
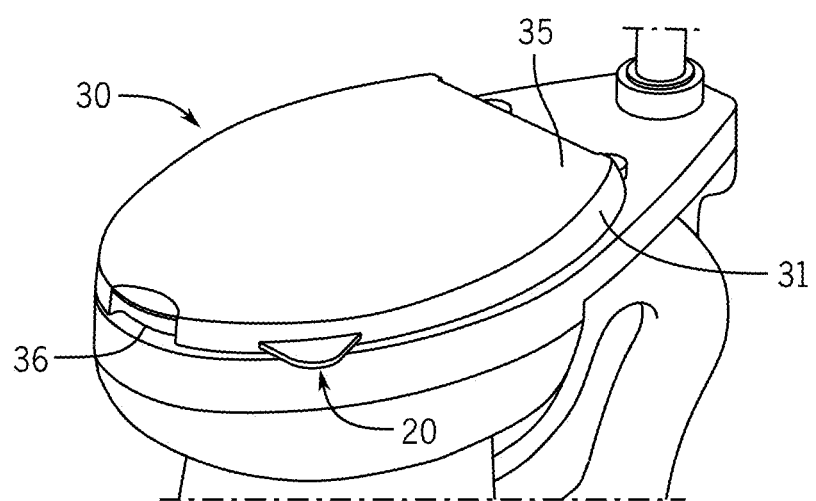
FIG. 36 is a perspective view of a toilet lid according to the eleventh embodiment of the present disclosure.
Figure 37:
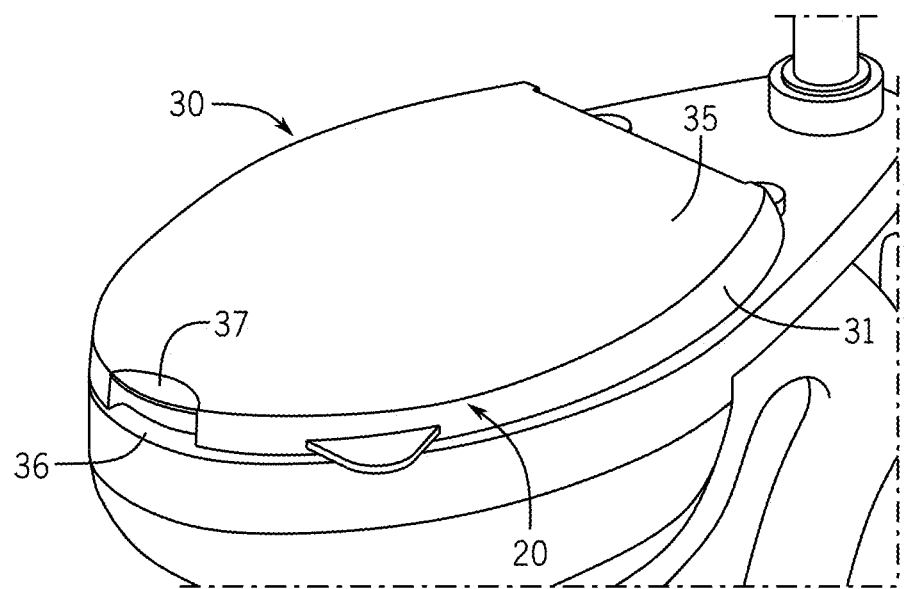
FIG. 37 is a perspective view of a variation of the toilet lid according to the eleventh embodiment of the present disclosure.

FIG. 36 is a perspective view of a toilet lid according to the eleventh embodiment of the present disclosure. FIG. 37 is a perspective view of a variation of the toilet lid according to the eleventh embodiment of the present disclosure.

Referring to FIG. 36, the toilet lid 30 according to this embodiment combines a concealment feature and any of the lifting features (e.g. touch point features) as disclosed in the first embodiment to tenth embodiment. For example, the lifting features may include the tab 20 disposed on the toilet seat 10 and/or the tab 40 disposed on the toilet lid 30.

As discussed above, the gap 12 in the toilet seat 10 leaves a space between the toilet lid 30 and the toilet bowl 50. Thus, in a current toilet in the art, the excrement particles containing the pathogens may escape from the space and spread in the form of the aerosols even when the toilet lid is in the closed status. Therefore, the current toilet in the art increases the risks for the users to get infected with the pathogens when the toilet is flushed.

According to this embodiment, the toilet lid 30 comprises a surface 35 and a rim 31 connected to the surface 35 so as to form a recessed area as the concealment feature. The recessed area may be in any shapes and dimensions that allow the toilet seat 10 to be received and sealed in the recessed area. In this embodiment, the recessed area may have substantially the same shapes and sizes as the toilet seat 10.

The rim 31 of the toilet lid 30 further comprises an opening at a position corresponding to the tab 20 disposed on the toilet seat 10. Thus, when the toilet lid 30 is closed, the toilet seat 10 may be received in the recessed area of the toilet lid 30 and the tab 20 may be extended from the opening of the toilet lid 30. Thus, the user may lift up the toilet seat 10 individually or together with the toilet lid 30 by using the tab 20.

The toilet lid 30 further comprises another lift feature disposed at the front end of the rim 31. The front end of the rim 31 is defined by an end facing the toilet user. The rim 31 is notched backwards so as to form a groove 36 as the lift feature. The groove 36 may be made of the antibacterial material, e.g. the copper material. Therefore, the groove 36 may become a touch point for the toilet users to open or close the toilet lid 30.

The copper material may be encapsulated into (e.g. distributing the copper particles throughout another material) or adhered to (e.g. surface coating on another material) the material of the tabs 20, 40, and/or the groove 36 of the toilet lid 30 (e.g. the plastic material). For example, when the copper material is adhered on the groove 36, an adhesive backed copper pad material may be placed directly on the groove 36. The copper material may be either visible or invisible to the toilet users. In another embodiment, the manufacturing processes may be similar to the first embodiment or the second embodiment as discussed earlier.

Referring to FIG. 37, the toilet lid 30 further comprises a recessed portion 37 disposed on the surface 35 and connected to the groove 36 on the rim 31. Thus, the recessed portion 37 may give the toilet users a visual indication as to the location of the lift feature, i.e. the groove 36.

When the toilet lid 30 is closed, the groove 36 offers a lift feature/touch point for the toilet users. Meanwhile, the toilet lid 30 functions as a shield configured to prevent the pathogens from escaping from the space between the toilet lid 30 and the toilet bowl 50 caused by the gap 12 of the toilet seat 10. Therefore, the risks for the users to get infected with the pathogens when the toilet is flushed may be further reduced.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

While this specification contains many specifics, these should not be construed as limitations on the scope of the invention or of what may be claimed, but rather as descriptions of features specific to particular embodiments of the invention. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

One or more embodiments of the disclosure may be referred to herein, individually and/or collectively, by the term "invention" merely for convenience and without intending to voluntarily limit the scope of this application to any particular invention or inventive concept. Moreover, although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

It is intended that the foregoing detailed description be regarded as illustrative rather than limiting and that it is understood that the following claims including all equivalents are intended to define the scope of the invention. The claims should not be read as limited to the described order or elements unless stated to that effect. Therefore, all embodiments that come within the scope and spirit of the following claims and equivalents thereto are claimed as the invention.

What is claimed is:

1. A toilet seat comprising:
a rim; and
a tab made from an antibacterial material and configured to be attached to the rim as a touch point for a user to open or close the toilet seat,
wherein the rim comprises a base disposed on a side of the rim,
wherein the base comprises a groove configured to receive the tab, and
wherein the tab comprises an insert portion configured to be inserted into the groove and comprises a grip portion connected to the insert portion and configured to be the touch point for the user.

2. The toilet seat according to claim 1,
wherein the rim further comprises a gap disposed at a front end of the rim,
wherein the front end of the rim is defined by an end facing the user,
wherein the gap is configured to receive a front seal of a toilet lid, and
wherein the front seal is disposed at a position corresponding to the gap.

3. The toilet seat according to claim 2,
wherein the toilet lid further comprises a front tab configured to be attached to the front seal, and
wherein the front tab extends forwards from the toilet lid in a substantially horizontal direction when the front tab is attached to the front seal.

4. A toilet comprising:
a toilet bowl;
a toilet seat comprising a rim and pivotably attached to the toilet bowl;
a toilet lid pivotably attached to the toilet bowl or the toilet seat; and
a first tab made from an antibacterial material and configured to be attached to the toilet seat as a first touch point for a user to open or close the toilet seat,
wherein the rim of the toilet seat comprises a base disposed on a side of the rim of the toilet seat,
wherein the base comprises a groove configured to receive the first tab, and
wherein the first tab comprises an insert portion configured to be inserted into the groove and comprises a grip portion connected to the insert portion and configured to be the first touch point for the user.

5. The toilet according to claim 4, further comprising a second tab made from an antibacterial material and configured to be attached to the toilet lid as a second touch point for the user to open or close the toilet lid,
wherein the first tab and the second tab are substantially aligned and spaced apart with each other when the first tab and the second tab are respectively attached to the toilet seat and the toilet lid.

6. The toilet according to claim 4,
wherein the rim of the toilet seat further comprises a gap disposed at a front end of the rim of the toilet seat,
wherein the front end of the rim of the toilet seat is defined by an end facing the user,
wherein the toilet lid comprises a front seal disposed at a position corresponding to the gap,
wherein the gap is configured to receive the front seal of a toilet lid, wherein the toilet lid further comprises a front tab configured to be attached to the front seal, and wherein the front tab extends forwards from the toilet lid in a substantially horizontal direction when the front tab is attached to the front seal.

\* \* \* \* \*